United States Patent [19]

Roberts et al.

[11] E Re. 29,634

[45] Reissued May 16, 1978

[54] DENTIFRICE CONTAINING VISIBLE AGGLOMERATED PARTICLES OF POLISHING AGENTS

[75] Inventors: Francis D. Roberts, West Millington, N.J.; John J. Steinke, III, Fayetteville, N.Y.

[73] Assignee: Colgate Palmolive Company, New York, N.Y.

[21] Appl. No.: 604,997

[22] Filed: Aug. 15, 1975

Related U.S. Patent Documents

Reissue of:

[64] Patent No.: 3,574,823
Issued: Apr. 13, 1971
Appl. No.: 750,028
Filed: Aug. 5, 1968

U.S. Applications:

[63] Continuation of Ser. No. 224,629, Feb. 8, 1972, abandoned.

[51] Int. Cl.[2] ..... A61K 7/18; A61K 7/22

[52] U.S. Cl. ..... 424/57; 424/49; 424/52; 424/54

[58] Field of Search ..... 424/48–58; 51/293–309

[56] References Cited

U.S. PATENT DOCUMENTS

| | | | |
|---|---|---|---|
| 1,082,681 | 12/1913 | Danner | 424/49 |
| 1,190,444 | 5/1933 | Nicholson | 51/308 |
| 1,528,543 | 3/1925 | Hartman | 51/308 |
| 1,965,299 | 7/1934 | Patterson | 51/308 |
| 2,010,910 | 8/1935 | Atkins | 424/49 |
| 2,024,146 | 12/1935 | Crowther | 424/49 |
| 2,196,150 | 4/1940 | Heald et al. | 424/57 |
| 2,196,154 | 4/1940 | Schulerud | 424/49 |
| 2,278,442 | 4/1942 | Hoany | 51/308 |
| 2,417,800 | 3/1947 | Weisser | 51/304 |
| 2,534,128 | 12/1950 | Howe | 51/304 |
| 2,534,129 | 12/1950 | Howe | 51/305 |
| 2,550,207 | 4/1951 | Tainter et al. | 424/49 |
| 2,681,274 | 6/1954 | Young | 51/305 |
| 2,820,000 | 1/1958 | Menzies | 424/49 |
| 2,829,035 | 4/1958 | Doughty | 51/304 |
| 2,877,103 | 3/1959 | Lane | 51/298 |
| 2,980,524 | 4/1961 | Morton | 51/293 |
| 3,003,919 | 10/1961 | Broge | 424/49 |
| 3,042,509 | 7/1962 | Soderberg | 51/305 |
| 3,070,510 | 12/1962 | Cooley et al. | 424/52 |
| 3,079,243 | 2/1963 | Ueltz | 51/298 |
| 3,151,027 | 9/1964 | Cooley et al. | 424/52 |
| 3,226,297 | 12/1965 | Ekenstam et al. | 424/49 |
| 3,265,475 | 8/1966 | Schantz | 51/304 |
| 3,325,368 | 6/1967 | Wood | 424/49 |
| 3,420,681 | 1/1969 | Karrup | 51/308 X |
| 3,450,813 | 6/1969 | Muhler | 424/52 |
| 3,538,230 | 11/1970 | Pader et al. | 424/50 |
| 3,574,823 | 4/1971 | Roberts et al. | 424/49 |
| 3,711,604 | 1/1973 | Colodney et al. | 424/52 |
| 3,803,301 | 4/1974 | Cordon et al. | 424/49 |
| 3,935,306 | 1/1976 | Roberts et al. | 424/49 |

FOREIGN PATENT DOCUMENTS

| | | |
|---|---|---|
| 1,381,416 | 11/1964 | France. |
| 954,281 | 12/1949 | France. |

OTHER PUBLICATIONS

Ronchi, "Optics–The Science of Vision" (1957), N.Y.U. Press, N.Y., N.Y., pp. 248–251, 254–255, 280–283.

Hartridge, "Recent Advances in the Physiology of Vision" (1950), Churchill, London, pp. 12–21, 106–127.

Luckiesh et al., "Seeing–A Partnership of Lighting and Vision" (1931), Williams & Wilkins, Baltimore, Md., pp. 24–57, 68–71, 84–85, Suppl. 1–5.

*Primary Examiner*—Shep K. Rose
*Attorney, Agent, or Firm*—Abner Sheffer

[57] ABSTRACT

Dentifrice containing visible, palpable and esthetically pleasing substantially water-insoluble agglomerated particles of polishing agents. The particles are reduced to smaller impalapable size by mild mechanical action such as by toothbrushing. The agglomerates include water-insoluble polishing agent such as insoluble sodium metaphosphate or dicalcium phosphate and may also contain a binding agent such as gum acacia, gelatin, starch, carboxymethyl cellulose or the like.

36 Claims, No Drawings

DENTIFRICE CONTAINING VISIBLE AGGLOMERATED PARTICLES OF POLISHING AGENTS

Matter enclosed in heavy brackets [ ] appears in the original patent but forms no part of this reissue specification; matter printed in italics indicates the additions made by reissue.

*This is a continuation of application Ser. No. 224,629 filed Feb. 8, 1972, now abandoned.*

This invention relates to novel dentifrice preparations containing visible, palpable and esthetically pleasing substantially water-insoluble agglomerated particles of polishing agent.

Dentifrices of the prior art commonly contain water-insoluble polishing agents which facilitate cleansing of the teeth. Since these agents are water-insoluble, they have been used in small particle sizes, substantially all of which are typically less than 177 microns in size and often even less than 10 microns. Such small sized particles help to avoid too much abrasiveness, palpability and retention of particles in the oral cavity even after rinsing which would be expected if larger particles of water-insoluble invisible, agent were employed. However, these small particles, being individually invisible, could not contribute to the esthetic appearance of the dentifrice.

It has now been found that dentifrice containing agglomerates of water-insoluble polishing agent of desirable polishing power can be prepared in a size visible to the naked eye which agglomerates are substantially water-insoluble and palpable, have desirable abrasiveness and are easily reduced to fine particle size upon being subjected to mild mechanical action, such as toothbrushing, so that the reduced size particles are easily cleared from the oral cavity. The agglomerates, being visible, contribute markedly to the visual and esthetic appeal of a dentifrice composition.

*The art-accepted limit of resolution of the human eye is about 100 micron. Thus the 1954 Edition, Guinness Book of World Records states:*

*"Smallest Visible Object*

*The resolving power of the human eye is... 1/60th of a degree..which corresponds to 100 microns at 10 inches..."*

*The book "Optics" by F.W. Sears of Massachusetts Institute of Technology, printed 1958, Addison-Wesley Publishing Co., at page 260 discusses "Limit of Resolution of the eye" and says that the distance (z) between "two just resolvable object points at the minimum distance of distinct vision... is about 1/10 mm"; 1/10 mm is 100 microns. And Civardi et al. U.S. Pat. No. 3,763,301 originally filed Dec. 9, 1968, at column 4 lines 57-62, states:*

*"The microporous materials... have pores invisible to the naked eye of a person with 20/20 vision. Such pores measure less than 100 microns in their maximum dimension (when a plane surface, such as the top or bottom of the material or a cross-section thereof is observed).*

*As mentioned above, it has been common in the toothpaste art to employ, as abrasives, impalpable particles of particle size well below 100 microns. For instance, Wood U.S. Pat. 3,325,368 of June 13, 1967 refers to the use of polishing agents of submicron size and says:*

*"In order to remove the plaque it is normal practice to use larger particles, having an average particle size usually between 5 and 20 microns".*

*Muhler U.S. Pat. No. 3,450,813 states (at column 6, lines 67-79):*

*"particles greater than 50 microns are gritty to the teeth and tongue and unsuitable for use in dentifrice compositions".*

*Toothpastes have also been made with agglomerates, aggregates or granulates of abrasive particles, such agglomerates, aggregates or granulates being of a size below the 100 micron limit of normal visibility. For instance the previously cited Wood patent describes "carrier particles" having "an average size in the range 1 to 50 microns, preferably 5 to 20 microns" having embedded therein abrasive particles having an average size of less than 1 micron, and Cooley et al. U.S. Pat. No. 3,151,027 describes toothpastes containing particles of hard mineral substances coated with a resin, states that "By particle is meant agglomerates as well as individual particles" (column 4, lines 65-66), and says that*

*"The coated particles should have a mean particle diameter in the range of about 2 microns to about 20 microns".*

*Broge U.S. Pat. No. 3,003,919 describes toothpastes containing alumina abrasives which are "porous agglomerates having structural rigidity" (column 5 lines 72-73); here again their size is well below the visible limit, 20 microns being the largest size mentioned (column 5 lines 52-67).*

It is an object of this invention to provide dentifrice preparations containing agglomerated particles of water-insoluble dental polishing agent which are easily reduced to fine size by mild mechanical action.

Other objects of the invention will be apparent from consideration of the following detailed description and claims.

In accordance with certain of the aspects, this invention relates to dentifrice comprising a dental vehicle and an agglomerated material containing water-insoluble polishing agent, particles of said agglomerated material being visible, said agglomerated material being palpable and substantially water-insoluble, and easily reducible to individual particles of polishing agent, each of which is fine, non-visible and non-palpable upon being subjected to mild mechanical action.

The agglomerated particles of polishing agent employed in the instant invention are present on the surface of and within a dentifrice. When the dentifrice is a transparent or translucent toothpaste, all agglomerated particles are visible to the naked eye. When it is opaque, the particles on the surface are visible. The particles are visibly distributed throughout a toothpowder also.

Translucent and transparent toothpastes as well as opaque toothpastes contain a dental vehicle which forms a gel or creamy mass of a consistency which can be desirably extruded from a collapsible tube such as an aluminum tube or a lead tube. The vehicle contains liquids and solids. In general, the liquid portion comprises water, glycerine, sorbitol, propylene glycol, polyethylene glycol 400 or the like including suitable mixtures thereof. It is usually advantageous to use a mixture of both water and a humectant, such as glycerine, sorbitol, propylene glycol or the like. The total liquid content is generally about 20–89.5% by weight of the toothpaste. In transparent and translucent toothpastes the liquid content of the toothpaste may be about 20–89.5% by weight while in opaque toothpastes the total liquid content is usually about 20–50%.

The solid portion of the vehicle is a gelling agent, such as the natural and synthetic gums and gum-like materials, such as Irish Moss, gum tragacanth, alkali metal carboxymethyl cellulose and hydroxymethyl carboxyethyl cellulose, polyvinyl pyrrolidone, starch, water soluble, hydrophilic colloidal carboxyvinyl polymers, such as those sold under the trademark Carbopol 934 and 940. The solid portion of the vehicle is typically present in an amount up to about 10% by weight of the toothpaste and preferably about 0.5–5% by weight.

The substantially water-insoluble agglomerated particles on the surface of and within the dentifrice contain a water-insoluble polishing agent and, in accordance with preferred embodiments of the invention, a binding agent.

Water-insoluble polishing agents of the prior art may be agglomerated in accordance with this invention. The polishing agents thus include insoluble phosphate salts, such as insoluble sodium metaphosphate, insoluble potassium metaphosphate, calcium pyrophosphate, magnesium orthophosphate, trimagnesium orthophosphate, tricalcium phosphate, dicalcium phosphate dihydrate, anhydrous dicalcium phosphate and the like. Other polishing agents include calcium carbonate, magnesium carbonate, hydrated alumina, silica, zirconium silicate, aluminum silicate including calcined aluminium silicate and polymethyl methacrylate. Combinations of polishing agents may be employed. The preferred polishing agents are the dicalcium phosphates and insoluble sodium metaphosphate.

The insoluble alkali metal metaphosphates are preferably the insoluble sodium and potassium salts of polymetaphosphoric acid. These materials are known in the art with the insoluble sodium metaphosphate having been suggested as a polishing agent as previously indicated. Such materials may be formed in any suitable manner, as illustrated by Thrope's Dictionary of Applied Chemistry, vol. 9 (4th ed.), pp. 510–511. The forms of insoluble sodium metaphosphate known as Madrell's salt and Kurrol's salt are further examples of suitable materials. These metaphosphate salts exhibit only a minute solubility in water, and are commonly referred to as insoluble metaphosphates, phosphates, therefore. There is present a minor amount of soluble phosphate material as impurities, usually of the order of a few percent such as up to about 4% by weight. The amount of soluble phosphate material which is believed to be a soluble sodium trimetaphosphate in the case of insoluble sodium metaphosphate may be reduced by washing with water if desired.

Binding agents which may be employed to assist formation of polishing agent into agglomerated particles include water-soluble materials such as gum acacia (arabic), geiatins, starches, alkali metal carboxymethyl cellulose, polyethylene glycols, glucose, sucrose, methyl cellulose, carboxyethyl hydroxymethyl celluloses, sodium alginate, polyvinyl pyrrolidone, polyvinyl alcohol, Irish Moss, gum tragacanth, magnesium aluminum silicate gel and the like. Mixtures of binding agents may be employed too. When the polishing agents are freed from binding with these agents upon application of mild pressure, typically a toothbrush applied in the oral cavity, these water-soluble agents are easily solubilized in saliva.

Typically, the polishing agent comprises about 75% - 100% by weight, preferably about 75%-98%, of the finished agglomerate. The binding agent when present preferably comprises about 2%-25% by weight of the finished agglomerate.

When employed the binding agent is blended with the polishing agent. The binding agent may be blended in dry powdered form of in solution in water or alcohol. The agglomerate may be formed in a dry process known as "slugging" or in a wet granulation process.

In the dry process or slugging process, the blend of polishing agent particles, substantially all of which typically have an individual particle size of less than 250 microns, and optionally binding agent, are compressed on a tablet press. The large tablet thereby formed typically has dimensions of about 6 mm. to 25 mm, although it may be even larger. The tablet is then broken into visible granule agglomerates having particles sizes, preferably up to about 2380 microns, most preferably about 420–840 microns, typically in a mill, granulator or comminutor.

When the dry or slugging process is employed, the blend to be agglomerated preferably also includes a lubricant such as talc, magnesium stearate, calcium stearate, stearic acid and the like. The lubricant facilitates agglomeration.

When dry powdered binder is blended with polishing agent in the wet granulation process, solvent, such as water or ethanol or a solution of additional binding agent, is contacted with the blend in sufficient amount to wet the mass.

The wet granulation process may be performed by wetting a powder blend of water-insoluble dental polishing agent particles typically having a particle size of less than 74 microns and binding agent in continuous contact on a Dravo pan, in a Hobart mixer or other suitable powder-wetting mixing device thereby forming a wet mass. The "wetting" may be performed by contact of the polishing agent with solid binder followed by moistening or with a solution of the binder.

The wet mass formed from the polishing agent and palpable agent is forced through a screen having uniform openings which may be from 420 microns to 2380 microns in size and dried as agglomerates. Typically in air or an oven. The agglomerates may then be segregated into desired sizes such as between 420 and 840 microns by passing through appropriately sized screens. It is noted that when the wet mass is formed in a Dravo pan, the forced screening may be unnecessary.

It is desirable that the agglomerate formed be easily introduced into the oral cavity in a dentifrice, such as a toothpaste, and comfortably maintained there until reduced in size during toothbrushing. Therefore, visible particles, generally having a particle size larger than about 2380 microns, are preferably separated from the agglomerates. In order to maximize the esthetic appearance of the agglomerates when they are incorporated into a dentifrice, it is desirable also to separate fines having a particle size smaller than about 420 microns. However, any agglomerates containing the components of the invention which are visible to the naked eye are within the scope of the invention.

If desired, the blend to be agglomerated, by wet or dry procedures, may also contain a non-abrasive diluent or filler, such as lactose, starch, mannitol, and the like, in amounts of about 1%-5% by weight of the agglomerate, in order to amelorate the polishing power of the agglomerate. Furthermore, the blend may include ancillary comonents, such as a color dye or pigment, particularly for an opaque toothpaste or a toothpowder. Typical dyes and pigments include F, D&C dyes and lakes and the like. Color material when employed, generally is present in amounts of 1-10%.

Due to the nature of the water-insoluble polishing agent which comprises the major proportion of the agglomerate, the agglomerate is characterized as being substantially water-insoluble. In the oral cavity it is quickly reduced in size from the visible, palpable aggiomerates introduced into individual invisible, fine, nonpalpable particles upon subjection to mild mechanical action, such as by rubbing on the teeth, gums or other portions of the oral cavity with a toothbrush, the tongue, a finger or the like.

The agglomerated particles are generally incorporated into a toothpaste in amount about 5–75% by weight of the dentifrice, preferably 10–75%. Typically, they comprise up to about 50% by weight of a transparent or translucent toothpaste.

In addition to the vehicle and agglomerates, the dentifrice may contain water-insoluble invisible polishing agent having a particle size typical of that employed in the prior art, such as less than about 74 microns, if it is desired to increase polishing power beyond that provided by the agglomerates.

The dentifrice may also contain surface-active agent. It is preferred that the total amount of surface-active agent be about 0.05–5% by weight, preferably about 1–3%, of the dentifrice. Surface-active agent may include water-soluble sulfates of compounds having long chain alkyl radicals (e.g. chains of 10 to 18 carbon atoms) are suitable. One preferred material is a long chain fatty acid monoglyceride sulfate, such as the sodium salt of hydrogenated coco fatty acid monoglyceride sulfate used along or in combination with sodium lauryl sulfate. Other suitable materials are the fatty acid amides of amino acids such as sodium N-lauroyl sarosinate.

Various other materials, may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%. Where coloring is employed, the agglomerates may be colored with a suitable contrasting color.

The toothpaste may also contain antibacterial agents in amounts of about 0.01–5%. Typical examples of such agents are guanidines, biguanides and amines such as:

$N^1$(4-chlorobenzyl)-$N^5$-2,4-dichlorobenzylbiguanide;
p-Chlorophenyl biguanide;
4-chlorobenzhydryl biguanide;
4-chlorobenzhydryl
N-3-lauroxypropyl-$N^5$-p-chlorobenzylbiguanide;
1,6-di-p-chlorophenylbiguanidohexane:
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
$N^5$-amino-1,3-bis(2-ethylhexyl)-5-methylhexahydropyrimidine;
and their non-toxic acid addition salts.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as sodium methylsalicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include spodium fluoride, stannous fluoride, potassium fluoride, potassium stannous fluoride ($SnF_2 \cdot KF$), sodium hexafluorostannate, stannous chlorofluoride, sodium fluorozirconate and sodium monofluorophosphate. These materials, which dissociate or release fluorine-containing ions in water, suitably may be present in an effective but nontoxic amount, usually within the range of about 0.01 to 1% by weight of the water soluble fluorine content thereof.

The toothpaste of the invention is formed by preparing a toothpaste containing no agglomerates and separately preparing the agglomerates in accordance with procedure set forth above. Thus, a gelling agent such as sodium carboxymethyl cellulose or Carbopol 934 and a preservative such as sodium benzoate, if employed, is dispersed with a humectant such as glycerine. Water may also be present. Additional humectant and water, as a 70% sorbitol solution, may then be mixed with the dispersion and heat is applied at about 40–60° C., say 50° C. to form a paste, gel or cream. Surface-active agent, such as sodium lauryl sulfate, if employed, is then dispersed in the mixture. The preparation is then deaerated and cooled. Desired flavor may then be added and the paste again deaerated.

The agglomerates are then dispersed in the toothpaste with minimal mechanical agitation, insufficient to substantially break them down. The toothpaste, including the esthetically pleasing substantially water-insoluble agglomerated particles of polishing agent, is then deaerated and tubed.

The following specific examples are further illustrative of the nature of the present invention, but it is understood that the invention is not limited thereto. The amounts and proportions of compositions described in the examples are by weight unless otherwise specified.

EXAMPLE I 220 parts of dicalcium phosphate dihydrate having an average particle size of about 4.2 microns are moistened with 91 parts of a 10% aqueous solution of gum acacia while blending the components in a Hobart mixer to uniformly wet the blend. The wet mass thereby formed is forced through a screen having uniform openings of 2380 microns and oven dried for 1 hour at 65° C. The dried agglomerates are then screened through a screen having uniform openings of 840 microns onto a screen having uniform openings of 420 microns. 132 parts of agglomerated dicalcium phosphate dihydrate are retained on the screen having uniform openings of 420 microns. 132 parts of agglomerated dicalcium phosphate dihydrate are retained on the screen having uniform openings of 840 microns and 37 parts pass through to the screen having uniform openings of 420 microns.

20 parts of the agglomerate particles which pass through the screen having uniform openings of 840 microns and which are retained on the screen having uniform openings of 420 microns are blended with 80 parts of a translucent toothpaste having the following formulation:

| | Percent |
|---|---|
| Water | 81.00 |
| Methyl parahydroxybenzoale | 0.15 |
| Propyl parahydroxybenzoate | 0.15 |
| Sodium saccharin | 0.20 |
| Clycerin | 10.00 |
| Carbopol 940 | 2.00 |
| Sodium lauryl sulfate | 1.50 |
| Sodium hydroxide solution (10%) | 5.00 |

Similar dentifrices may be formed using aggregates formed by blending with a 10% gum acacia solution; hydrated alumina having an average particle size less than about 2.5 microns; calcium carbonate having particles substantially all of which are less than about 7.4 microns in size; anhydrous dicalcium phosphate having particles substantially all of which are less than about 7.4 microns in size; and insoluble sodium metaphospate having an average particle size of about 4.8 microns.

The toothpastes described in this example are translucent and esthetically pleasing. There are dispersed in the toothpaste visible particles of the agglomerate polishing agents. During tooth brushing the agglomerated particles are at first palpable and are then easily reduced to individual particles of polishing agent of fine size upon application of mild pressure with the toothbrush.

EXAMPLE II 6000 parts of anhydrous dicalcium phosphate particles having sizes indicated in Example I are blended with 150 parts of gum arabic powder and 50 parts of gum tragacanth. The blend is then moistened with a 10 % aqueous solution of gum arabic. The agglomerates are then formed and screened in the manner set forth in Example I.

20 parts of the agglomerate particles described above are blended with 80 parts of a transparent toothpaste having the following formulation.

| | Percent |
|---|---|
| Glycerine | 10.00 |
| Sodium carboxymethyl cellulose | 2.00 |
| Sodium benzoate | 0.50 |
| Sodium saccharin | 0.20 |
| Sodium lauryl sulfate | 2.50 |
| Color | 0.10 |
| Ethanol (95%) | 10.00 |
| Flavor | 1.30 |
| Sorbitol solution (70%) | 73.40 |

Similar dentifrices may be formed using aggregates in which the anhydrous dicalcium phosphate, gum arabic powder and gum tragacanth are moistened with (A) a 20% solution of gum arabic, (B) a 10% solution of polyvinyl pyrrolidone, (C) water, (D) ethanol or (E) glucose solution.

The toothpastes described in this example are translucent and esthetically pleasing. There are dispersed in the toothpastes visible particles of the agglomerate polishing agents. During toothbrushing the agglomerated particles are at first palpable and are then easily reduced to individual particles of polishing agent of fine size upon application of mild pressure with the toothbrush.

EXAMPLE III

Agglomerates indicated below are made by blending polishing agent, binder and lubricant to form a powder blend. The powder blend is compressed in a rotary tablet press to form slugs about 6 mm. × 25 mm. in size. The slugs are then granulated in an oscillating granulator to form smaller particles. These particles are screened with screens having uniformly spaced openings of 840 microns and 420 microns. 116 parts have particle sizes greater than 840 microns and 266 parts have particle sizes between 420 microns and 840 microns. The remaining agglomerates are finer than 420 microns.

Agglomerates are made by slugging blends of the following components:

| | Parts | | | | | | | | | |
|---|---|---|---|---|---|---|---|---|---|---|
| | (A) | (B) | (C) | (D) | (E) | (F) | (G) | (H) | (I) | (J) |
| Polishing agent: | | | | | | | | | | |
| Dicalcium phosphate dihydrate | 890 | | | | | | | 910 | | |
| Calcium carbonate | | 440 | | | | | 865 | | | |
| Insoluble sodium metaphosphate | | 450 | | | 845 | 865 | | | | 900 |
| Hydrated alumina | | | 500 | 790 | | | | | 500 | |
| Binder: Polyethylene glycol 6000 | 100 | 100 | 100 | 200 | 100 | 100 | 100 | 130 | 100 | 100 |
| Lubricant: | | | | | | | | | | |
| Magnesium stearate | 10 | 10 | 10 | 10 | | | | 10 | 10 | |
| Talc | | | | | 35 | 35 | 35 | | | |
| Stearic acid | | | | | | 5 | | | | |

20 parts of each of the agglomerate particles described above are blended with 80 parts of a transparent toothpaste having the following formulation:

| | Percent |
|---|---|
| Glycerine | 10.00 |
| Sorbitol solution (70%) | 75.10 |
| Sodium benzoate | 0.50 |
| Sodium carboxymethyl cellulose | 2.00 |
| Sodium lauryl sulfate | 1.50 |
| Flavor | 0.80 |
| Ethanol (95%) | 10.00 |
| Color | 0.10 |

The toothpastes described in this example are translucent and esthetically pleasing. There are dispersed in the toothpastes visible particles of the agglomerate polishing agents. During toothbrushing the agglomerated particles are at first palpable and are then easily reduced to individual particles of polishing agent of fine size upon application of mild pressure with the toothbrush.

EXAMPLE IV 99 parts of unmilled dicalcium phosphate dihydrate having an average particle size of about 118±33 microns are blended with 1 part of magnesium stearate lubricant. The powder blend is compressed on a rotary tablet press to form agglomerate slugs 6 mm. × 25 mm. in size. The slugs are then granulated in an oscillating granulator to form smaller agglomerate particles. These particles are screened with screens having uniformly spaced openings of 840 microns and 420 microns. 20 parts of the agglomerate particles which pass through the screen having uniform openings of 840 microns and which are retained on the screen having uniform openings pf 420 microns are blended with 80 parts of a translucent toothpaste having the following formulation:

| | Percent |
|---|---|
| Glycerin | 10.000 |
| Sorbitol (70%) | 74.075 |
| Sodium carboxymethyl cellulose | 2.000 |
| Sodium benzoate | 0.500 |
| Sodium saccharin | 0.200 |
| Color | 0.100 |
| Sodium lauryl sulfate | 1.500 |
| Ethanol (95%) | 10.000 |
| Flavor | 1.625 |

The toothpaste described in this example is translucent and esthetically pleasing. There are dispersed in the toothpaste visible particles of the agglomerate polishing agents. During toothbrushing the agglomerated particles are at first palpable and are then easily reduced to individual particles of polishing agent of fine size upon application of mild pressure with the toothbrush.

EXAMPLE V 200 parts of anhydrous dicalcium phosphate particles having sizes substantially all of which are less than about 7.4 microns and 1 part of D&C Lake Red No. 30 color, are moistened with 40 parts of a 10% aqueous solution of gum acacia in a Hobart mixer for 10 minutes. The dyed wet mass thereby formed is forced through a screen having uniform openings of 2380 microns and oven dried for 1 hour at 65° C. The dried agglomerates are then screened through a screen having uniform openings of 840 microns onto a screen having uniform openings of 420 microns.

10 parts of the dyed agglomerate particles which pass through the screen having uniform openings of 840 microns and which are retained on the screen having uniform openings of 420 microns are blended with 90 parts of an opaque toothpaste having the following formulation:

| | Percent |
|---|---|
| Glycerine (99.3%) | 19.950 |
| Sodium carboxymethyl cellulose | 0.850 |
| Sodium saccharin | 0.200 |
| Sodium benzoate | 0.500 |
| Tetrasodium pyrophosphate | 0.250 |
| Water | 19.986 |
| Trimagnesium phosphate | 0.200 |
| Calcium carbonate | 5.000 |
| Dicalcium phosphate dihydrate | 46.550 |
| Sodium N-lauroyl sarcosinate (35%) | 5.714 |
| Flavor | 0.800 |

The opaque toothpaste described in this example has visible particles of the agglomerates distributed over its surface. During toothbrushing the agglomerated particles are at first palpable and are then easily reduced to individual particles of polishing agent of fine size upon application of mile pressure with the toothbrush.

Although this invention has been described with reference to specific examples, it will be apparent to one skilled in the art that various modifications may be made thereto which fall within its scope.

We claim:

1. A *transparent* toothpaste comprising (I) a dental vehicle comprising water, a humectant and a gelling agent and (II) about 5–75% by weight of said *transparent* toothpaste of visible, palpable particles of substantially water-insoluble agglomerated material consisting essentially of material selected from the group consisting of (a) water-insoluble dental polishing agent; (b) mixtures of about 75–98% by weight of water-insoluble dental polishing agent with (b–1) water-soluble binding agent, (b–2) water-soluble binding agent and a lubricant, (b–3) water-soluble binding agent and a non-abrasive diluent, and (b–4) water-soluble binding agent, a lubricant and a non-abrasive diluent; and (c) mixture of about 99% by weight of water-insoluble dental polishing agent with a lubricant.

2. The toothpaste claimed in claim 1 wherein said particles of agglomerated material have particle sizes between 420 microns and 840 microns.

3. The toothpaste claimed in claim 1 wherein said water-insoluble polishing agent is dicalcium phosphate.

4. The toothpaste claimed in claim 1 wherein said [toothpaste is transparent and said] dental vehicle has a liquid content of water and humectant of about 20–89.5% by weight of said toothpaste.

5. The toothpaste claimed in claim 4 wherein said dental vehicle contains as humectant sorbitol and as gelling agent sodium carboxymethyl cellulose.

6. The toothpaste claimed in claim 1 wherein said substantially water-insoluble agglomerated material consists essentially of a mixture of about 75–98% by weight of water-insoluble dental polishing agent with water-soluble binding agent, water-soluble binding agent and a lubricant, water-soluble binding agent and a non-abrasive diluent, or water-soluble binding agent, a lubricant and non-abrasive diluent.

7. The toothpaste claimed in claim 6 wherein said water-insoluble dental polishing agent is calcium carbonate.

8. The toothpaste claimed in claim 6 wherein said water-insoluble dental polishing agent is hydrated alumina.

9. The toothpaste claimed in claim 6 wherein said water-soluble binding agent is gum acacia.

10. The toothpaste claimed in claim 6 wherein said water-soluble binding agent is polyvinyl pyrrolidone.

11. The toothpaste claimed in claim 6 wherein said water-soluble binding agent is polyethylene glycol.

12. The toothpaste claimed in claim 11 wherein said substantially water-insoluble agglomerated material consists essentially of a mixture of about 75-98% by weight of water-insoluble dental polishing agent with water-soluble polyethylene glycol binding, agent and a lubricant or with water-soluble polyethylene glycol binding agent, a lubricant and a non-abrasive diluent.

13. The toothpaste claimed in claim 6 wherein said water-insoluble dental polishing agent comprises an insoluble phosphate salt.

14. The toothpaste claimed in claim 13 wherein said insoluble phosphate salt is insoluble sodium metaphosphate.

15. The toothpaste claimed in claim 13 wherein said insoluble phosphate salt is dicalcium phosphate.

*16. A speckled transparent toothpaste comprising (I) a transparent dental vehicle including water, humectant and a gelling agent, and, blended therewith and dispersed therein, (II) individually visible palpable particles of sub-*

*stantially water-insoluble agglomerated material consisting essentially of individually invisible impalpable water-insoluble agglomerated powder particles of dental polishing agent, said powder particles being so agglomerated that said visible palpable particles retain their visibility and palpability in the toothpaste but are mechanically reduced to impalpability when the toothpaste is rubbed on the teeth during brushing with a toothbrush, the maximum amount of said palpable particles being about 75 percent by weight and the amount of said palpable particles being such that said toothpaste when viewed with the naked eye has the visual effect of having said palpable particles distributed therein, the content of dental polishing agent in said toothpaste being sufficient to provide a dental polishing action on use of said toothpaste, said toothpaste when viewed with the naked eye having the visual effect of being speckled by virtue of having said palpable particles distributed in said transparent vehicle.*

*17. Toothpaste as in claim 16 wherein said visible palpable particles are of a size to pass through a screen having uniform openings of 840 microns.*

*18. Toothpaste as in claim 16 wherein said agglomerated material further includes an agglomerating agent which is a binding agent or lubricant.*

*19. Toothpaste as in claim 18 wherein said agglomerated material further includes a non-abrasive diluent.*

*20. Toothpaste as in claim 16 wherein said agglomerated material further includes up to 10 percent by weight of a color dye or pigment.*

*21. Toothpaste as in claim 16 wherein said water-insoluble polishing agent constitutes the major portion of said agglomerated material.*

*22. Toothpaste as in claim 17 containing water-insoluble invisible polishing agent of particle size less than about 74 microns to increase polishing power beyond that provided by said agglomerated powder.*

*23. Toothpaste as in claim 17 in which said visible palpable particles contain agglomerated powder particles of zirconium silicate polishing agent.*

*24. Toothpaste as in claim 23 in which water-insoluble polishing agent constitutes the major portion of said agglomerated material.*

*25. Toothpaste as in claim 18 in which the agglomerating agent comprises polyethylene glycol 6000.*

*26. Toothpaste as in claim 18 in which the agglomerating agent comprises steric acid.*

*27. A toothpaste as in claim 16 in which the amount of said palpable particles is up to about 50% by weight of said toothpaste and said visible palpable particles are of a size to pass through a screen having uniform openings of 840 microns.*

*28. A toothpaste as in claim 16 wherein said water-insoluble polishing agent constitutes the major portion of said agglomerated material, said toothpaste containing water-insoluble invisible polishing agent of particle size less than about 74 microns to increase polishing power beyond that provided by said agglomerated powder.*

*29. A transparent toothpaste comprising (I) a transparent dental vehicle including water, humectant and a gelling agent and, blended therewith and dispersed therein, (II) individually visible palpable particles of substantially water-insoluble agglomerated material consisting essentially of individually invisible, impalpable water-insoluble agglomerated powder particles of dental polishing agent, said powder particles being so agglomerated that said visible palable particles retain their visibility and palpability in the toothpaste but are mechanically reduced to impalpability when the toothpaste is rubbed on the teeth during brushing with a toothbrush, the amount of said palpable particles being such that said toothpaste when viewed with the naked eye has the visual effect of having all said palpable particles visibly distributed in said transparent vehicle, the content of dental polishing agent in said toothpaste being sufficient to provide a dental polishing action on use of said toothpaste, the amount of said water and humectant in said toothpaste being about 20 to 89.5% by weight of said toothpaste.*

*30. A toothpaste as in claim 29 wherein said water-insoluble polishing agent constitutes the major portion of said agglomerated material, said toothpaste contains water-insoluble invisible polishing agent of particle size less than about 74 microns to increase polishing power beyond that provided by said agglomerated powder, said dental vehicle is transparent and said toothpaste when viewed with the naked eye has the visual effect of being speckled by virtue of having said palpable particles distributed therein, the amount of said palpable particles being up to about 50% by weight of said toothpaste.*

*31. A toothpaste as in claim 16 in which said palpable particles are products prepared by a process in which pre-existing dry impalpable dental polishing agent powder articles are agglomerated together.*

*32. A toothpaste as in claim 31 in which said process comprises mixing said impalpable powder particles with an agglomerating agent which is a binding agent or lubricant.*

*33. A toothpaste as in claim 32 in which said agglomerating agent is a water-soluble binding agent.*

*34. Toothpaste as in claim 32 in which said agglomerating agent is a lubricant.*

*35. Toothpaste as in claim 32 in which said process comprises mixing said powder particles with said agglomerating agent to form a mass larger than said palpable particles and then subdividing said mass into said palpable particles.*

*36. A toothpaste comprising (I) a dental vehicle including water, humectant and a gelling agent, and, blended therewith and dispersed therein, (II) individually visible palpable particles of substantially water-insoluble agglomerated material consisting essentially of individually invisible, impalpable water-insoluble agglomerated powder particles of dental polishing agent, said powder particles being so agglomerated that said visible palpable particles retain their visibility and palpability in the toothpaste but are mechanically reduced to impalpability when the toothpaste is rubbed on the teeth during brushing with a toothbrush, the maximum amount of said palpable particles being about 75 percent by weight and the amount of said palpable particles being such that said toothpaste when viewed with the naked eye has the visual effect of having said palpable particles distributed therein, the content of dental polishing agent in said toothpaste being sufficient to provide a dental polishing action on use of said toothpaste, said impalpable powder particles being particles less than 10 microns in diameter and said dental vehicle being transparent or translucent so that all said agglomerated particles are visible to the naked eye.*

* * * * *